United States Patent [19]

Oude Alink et al.

[11] 4,022,785

[45] May 10, 1977

[54] SUBSTITUTED PYRIDINES AND DIHYDROPYRIDINES

[75] Inventors: Bernardus A. Oude Alink, St. Louis; Neil E. S. Thompson, Creve Coeur, both of Mo.

[73] Assignee: Petrolite Corporation, St. Louis, Mo.

[22] Filed: Jan. 8, 1976

[21] Appl. No.: 647,342

[52] U.S. Cl. .................. 260/290 P; 260/296 H; 252/390
[51] Int. Cl.² ............. C07D 213/02; C07D 213/06
[58] Field of Search ................ 260/290 P, 296 H

[56] References Cited
UNITED STATES PATENTS 3,931,191  1/1976  Alink .................. 260/290 P

OTHER PUBLICATIONS

Raphael et al., Advances in Organic Chemistry, Methods and Results, vol. 5, Interscience Pub., pp. 6 and 39.

*Primary Examiner*—Alan L. Rotman
*Attorney, Agent, or Firm*—Sidney B. Ring; Hyman F. Glass

[57] ABSTRACT

This invention relates to a process of preparing alkylpyridines and N-substituted alkyldihydropyridines from hexahydrotriazines. These products may be further reacted to form other compositions. The products of the reaction are useful as corrosion inhibitors.

12 Claims, 1 Drawing Figure

1  REACTOR
2  SCRUBBER
3  STORAGE & DISPOSAL SYSTEM
4  FEED LINE FOR HEXAHYDROTRIAZINE
5  FEED LINE FOR CATALYST
6  AMMONIA GAS
7  OFF-GAS VENT LINE
8  FEED LINE FOR ALDEHYDE
9  FEED LINE FOR MAKE UP AMMONIA
10  AQUEOUS PHASE
11  HEXAHYDROTRIAZINE LINE
12  RECOVERED ALDEHYDE & HEXAHYDROTRIAZINE
13  WATER DISPOSAL
14  PRODUCT REMOVAL LINE

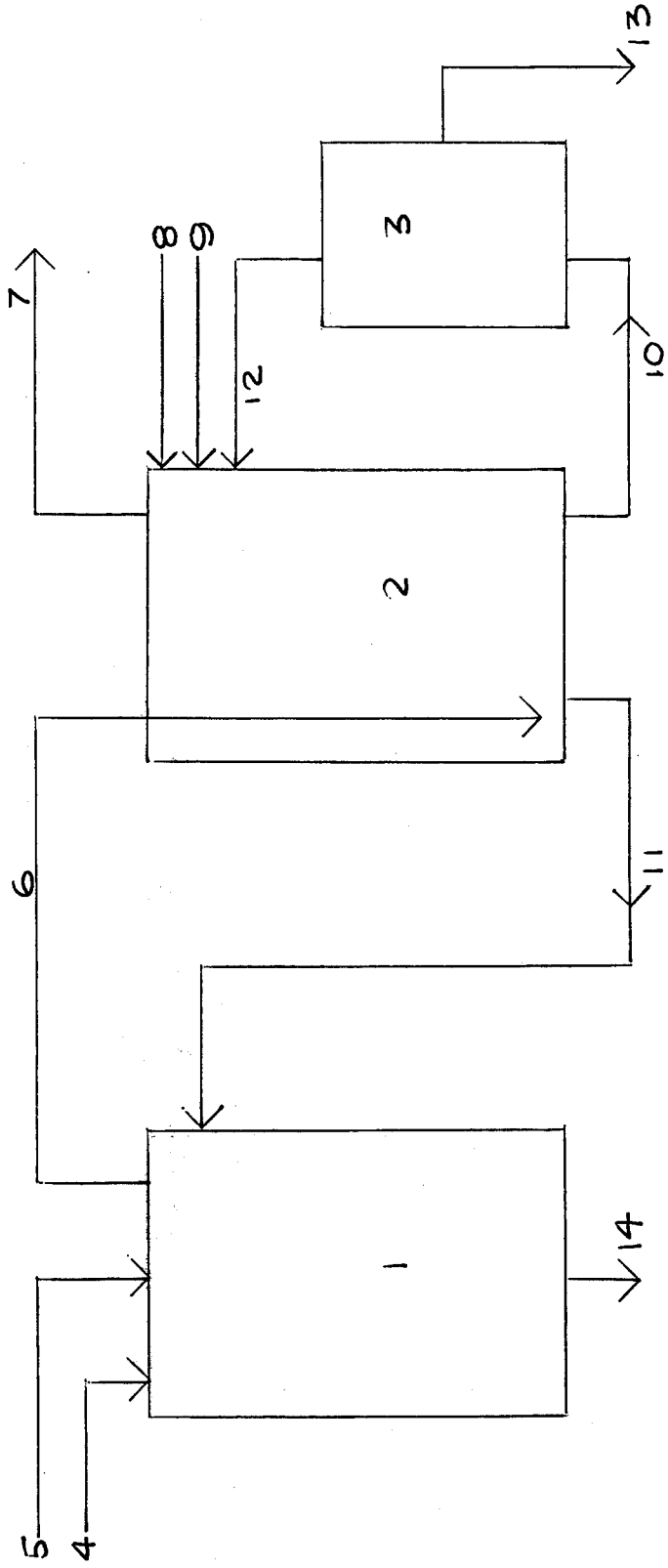
Process Flow Sheet
1 REACTOR
2 SCRUBBER
3 STORAGE & DISPOSAL SYSTEM
4 FEED LINE FOR HEXAHYDROTRIAZINE
5 FEED LINE FOR CATALYST
6 AMMONIA GAS
7 OFF-GAS VENT LINE
8 FEED LINE FOR ALDEHYDE
9 FEED LINE FOR MAKE UP AMMONIA
10 AQUEOUS PHASE
11 HEXAHYDROTRIAZINE LINE
12 RECOVERED ALDEHYDE & HEXAHYDROTRIAZINE
13 WATER DISPOSAL
14 PRODUCT REMOVAL LINE

SUBSTITUTED PYRIDINES AND DIHYDROPYRIDINES

We have discovered a novel process of preparing alkylpyridines and N-substituted alkyldihydropyridines from hexahydrotriazines.

The process involves the formulation of hexahydrotriazines from aldehydes and ammonia and, under the influence of a catalyst, thermally reacting the hexahydrotriazines to yield mixtures of alkylpyridines and N-substituted alkyldihydropyridines. The mixture obtained in this way may be further reacted to form (a) mixtures of alkylpyridines and N-substituted alkylpyridinium salts, (b) mixtures of alkylpyridines and amines or (c) alkylpyridines.

Aldehydes,

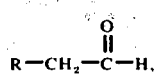

and ammonia react to form hexahydrotriazines according to the equation:

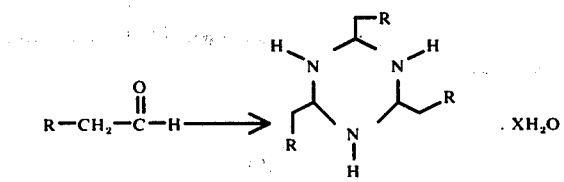

We have discovered that when reacted in the presence of a Lewis acid catalyst, hexahydrotriazines yield a mixture of alkylpyridines and N-substituted alkyldihydropyridines. The initial product is an unstable dihydropyridine formed according to the following equation:

Equation 2

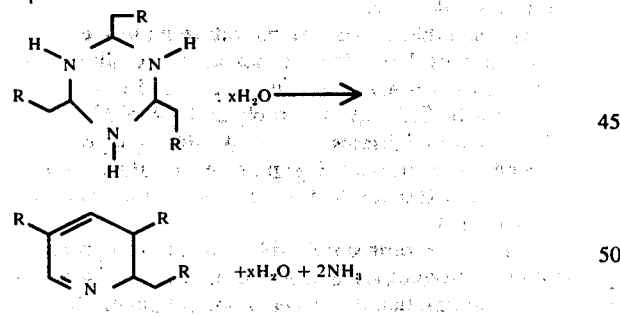

This dihydropyridine then reacts with the starting material in a disproportionation reaction to yield an alkylpyridine and an amine according to the equation:

Equation 3

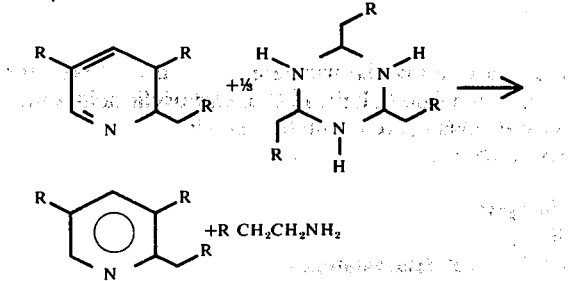

The amine then reacts with the starting hexahydrotriazine to yield an N-substituted alkyldihydropyridine which under reaction conditions is stable according to the equation:

Equation 4

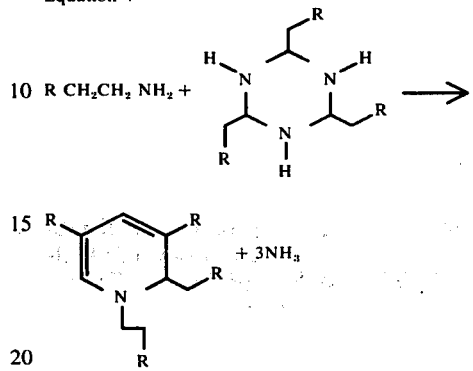

The overall reaction equation may be written as follows:

Equation 5

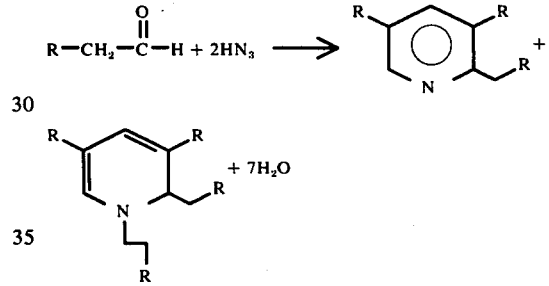

This reaction product may be further modified by a. reacting the final reaction product, in the presence of an acid, with air to yield an alkylpyridine and an N-substituted alkylpyridinium salt according to the equation:

Equation 6

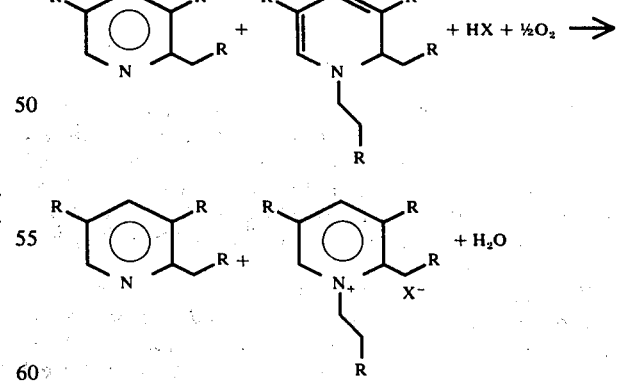

where HX is an acid, including organic and inorganic acids, for example, sulfuric acids, halogen acids such as hydrochloric, hydrobromic, and organic acids such as acetic, proprionic, benzoic, sulfonic acids, etc.

b. thermally reacting the alkylpyridine and alkylpyridinium salt to yield an alkylpyridine according to the equation:

Equation 7

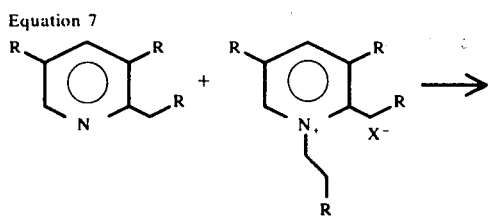

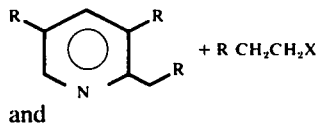

and c. reacting the mixture of alkylpyridine and N-substituted alkyldihydropyridine to yield a mixture of alkylpyridine and the Diels-Alder dimer of the dihydropyridine according to the equation:

Equation 8

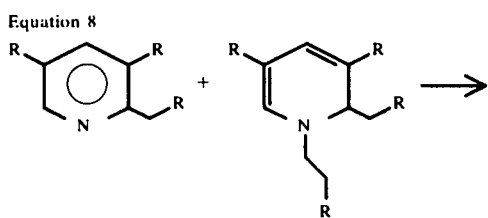

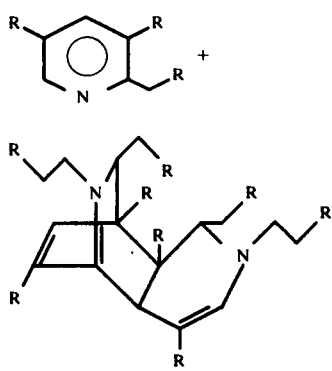

R in the above equations corresponds to the R of the aldehyde described below as

The reaction can be carried out in two different ways. In the first method a mixture of the hexahydrotriazine and aldehyde and pre-reacted in the presence of a weak Lewis acid catalyst with the removal of the water produced. The disadvantage of this process is that side reactions such as aldol condensation of the aldehyde can take place.

The second method comprises heating the hexahydrotriazine. The ammonia gas evolved in this reaction can be collected in a scrubber system. It is advantageous to collect the ammonia gas in a scrubber system containing the aldehyde. In this way the hexahydrotriazine can be produced from the ammonia produced. An outline of a manufacturing process is shown in the process flow sheet of the drawing.

The process flow sheet may be described as follows.

The hexahydrotriazine is prepared in the Scrubber 2 by addition of aldehyde through 8 to aqueous ammonia. The reaction mass is allowed to settle in 2 and the aqueous phase is drawn off through 10 to a storage vessel 3. The hexahydrotriazine is charged to the reactor 1 through 4 and the catalyst is added through 5. The aqueous phase is drawn off through 10 from 2 to the storage and disposal system 3. Aldehyde is added through 8 and recovered aldehyde and hexahydrotriazine are added to 2 through 12. Make up ammonia is added through 9. The reactor 1 is heated and ammonia and condensate are fed through 6 into the Scrubber 2 where reaction takes place to form the hexahydrotriazine. Hexahydrotriazine formed in 2 is added to 1 through 11. The non-adsorbed gases are vented through 7. After completion of the reaction the product is removed through 14. The process can then be repeated again. The water produced in the reaction is removed by decreasing its volume in 3 where after treatment so as not to interfere with the ecology, water is disposed off through 13.

Any suitable aldehyde can be employed, i.e., any aldehyde having a

group except acetaldehyde. This includes aldehydes of the formula

where R is alkyl, aryl, cycloalkyl, alkaryl, aralkyl, heterocyclic, etc. R is preferably alkyl, for example having from 1 to 30 or more carbons such as from 1 to 18 carbons, but preferably from about 1 to 12 carbons. The R in the above equation corresponds to the R of the aldehyde.

These include proprionaldehyde, butyraldehyde, heptaldehyde, etc., as well as substituted aldehydes, such as aldol, etc.

Any suitable reaction temperature may be employed. In practice, the hydrotriazines are generally prepared at relatively low temperatures such as from about 20° to about 70° C, but preferably at 10°–35° C.

The alkyl pyridines and N-alkyldihydropyridines are generally prepared at higher temperatures, such as from about 80° to 300° C, but preferably from about 110° to 180° C.

The reaction time should be sufficient to prepare the desired product such as from about 0.5 to 24 hours or more. In practice, these reactions are generally carried out for about 2 to 4 hours.

The catalyst employed is of the Lewis Acid type. Typical catalysts include salts, such as inorganic and organic acids, for example ammonia or amine salts of the general formula

where 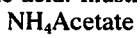 is ammonia or amine and X is an anion, for example a halide (Cl, Br, F, I) or carboxylic acid, sulfuric acid. Illustrative examples include NH$_4$Acetate
NH$_4$ Cl
NH$_4$ Br
NH$_4$ I
NH$_4$ benzenesulfonate, etc.

Zinc halide such as zinc chloride, silica, etc. Other catalysts include $AlCl_3$, $FeCl_3$, PbO, $Al_2O_3$, etc.

The following examples are presented for purposes of illustration and not of limitation.

EXAMPLE 1

1-Butyl, 2-propyl,3,5-diethyl 1,2-dihydropyridine and 2-propyl 3,5-diethylpyridine.

To a cooled aqueous 28% ammonia solution (1500 cc) was added 1000 cc butyraldehyde at such a rate that a temperature of $\leq 35°$ C. was maintained. The mixture was stirred for 2 hours and the two resulting layers were separated, in an aqueous phase and an organic layer (750 grams). The organic layer was identified as 2,4,6-tripropyl 1,3,5 hexahydrotriazine, containing 1 mole of water.

Anal. calc.ed for $C_{12}H_{27}N_3$, $H_2O$: N, 18.2. Found: N, 17.9.

$C^{13}$ magnetic resonance spectrum; solvent $CDCl_3$, $\delta$ in ppm. 73.6, d, (] = 140.7 Hz; 42.5, t,(] = 125.0 Hz); 21.7, t, (] = 124.0 Hz; and 17.4, g, (125.0 Hz). A reaction vessel was charged with 197 grams of 2,4,6-tripropyl 1,3,5-hexahydrotriazine and 1.5 grams of acetic acid. The mixture was slowly heated, with stirring over a 1½ hour period to 180° C. During this period copious evolution of ammonia gas took place; low boiling products, mainly water, were removed during the reaction. The resulting 140 grams of product was separated by preprative gas chromatography in two major components. The products were identified as 2-propyl 3,5-diethylpyridine. Anal. Calc.ed for $C_{12}H_{19}N$, N 7.91; Found, N 7.85. $C^{13}$ magnetic resonance spectrum, solvent $CDCl_3$, $\delta$ in ppm, 157.2; 146.1; 136.5; 135.4; 146.1; 36.5; 25.8; 25.2; 22.9; 15.3; 14.9 and 14.2, and 1-Butyl, 2-pyropyl, 3,5-diethyl 1,2-dihydropyridine. Anal. Calc.ed for $C_{16}H_{29}N$; N, 5.96; found N, 5.81, nuclear magnetic resonance spectrum 5.61, m, 2H; 3.59, m, 1H; 2.87 t, 2H; g, 4H 1.33, m, and 1.01 t, 18H; $C^{13}$ magnetic resonance spectrum. $\delta$ in ppm. Solvent $CDCl_3$, 128.2; 128.0; 119.7; 111.4; 60.2; 54.2; 34.3; 32.4; 27.7; 25.6; 20.1; 18.8; 14.9; 14.6; 14.0; and 12.6.

EXAMPLE 2

N-Butyl, 2-propyl 3,5-diethylpyridinium acetate and 2-Propyl 3,5-diethylpyridine.

To a mixture of 140 grams of 1-Butyl, 2-propyl, 3,5-diethyl 1,2-dihydropyridine and 2-propyl 3,5-diethylpyridine prepared as described in example 1 was added 18 grams of acetic acid, the mixture was stirred for 18 hours at ambient temperature in the presence of air. The resulting reaction product was extracted with water. The water insoluble fraction was identified as 2-propyl 3,5-diethylpyridine. The aqueous extract was evaporated under diminished pressure to yield 71 grams of N-Butyl, 2-propyl, 3,5-diethylpyridinium acetate, nuclear magnetic resonance spectrum, solvent $CCl_4$. $\delta$ in ppm, 9.20 m, 1H; 8.33, m, 1H; 4.78 m, 2H; 2.95, m, 6H; 1.80 s, 3H; 1.33, m, and 0.99 m, 18H.

EXAMPLE 3

2-Propyl 3,5-diethylpyridine.

To a mixture of 140 grams of 1-butyl, 2-propyl 3,5-diethyl 1,2-dihydropyridine and 2-propyl 3,5-diethylpyridine, prepared as described in example 1, was added 18 grams of acetic acid and the mixture was stirred in the presence of air for 18 hours. The resulting product was heated to reflux with removal of volatile materials (mainly butylacetate), and refluxed for 8 hours, to yield 123 grams of 2-propyl 3,5-diethylpyridine.

EXAMPLE 4

Dimer of 1-Butyl, 2-propyl, 3,5-diethyl, 1,2-dihydropyridine and 2-propyl 3,5-diethylpyridine.

A mixture of 140 grams of 1-butyl 2-propyl 3,5-diethyl 1,2-dihydropyridine and 2-propyl 3,5-diethylpyridine prepared as described in example 1 was heated for five hours at 245° C. Analyses of the resulting product were consisted with a mixture of 2-propyl, 3,5-diethylpyridine and the Diels-Alder dimer of 1-butyl, 2-propyl 3,5-diethyl 1,2-dihydropyridine.

EXAMPLE 5

1-Butyl 2-propyl 3,5-diethyl 1,2-dihydropyridine and 2-propyl 3,5-diethylpyridine.

To 360 grams of 2,4,6-tripropyl 1,3,5-hexahydrotriazine was added 3 grams of ammonium chloride and 720 grams of butyraldehyde. The mixture was heated over a 3 hour period to 180° C while the volatile material was removed by distillation. The resulting product 845 grams of material was separated in three components, 12% of 2-ethylhex-2-enal; 30% of 1-butyl 2-propyl 3,5-diethyl 1,2-dihydropyridine, and 58% of 2-propyl 3,5-diethylpyridine.

EXAMPLE 6

1-Butyl-2-propyl 3,5-diethyl 1,2-dihydropyridine and 1-propyl 3,5-diethylpyridine.

As outlined in the drawing to a scrubber was charged 100cc of 28% aqueous ammonia and butylaldehyde, 81 grams, was added maintaining a temperture of $\leq 35°$ C. The phases were allowed to separate. The aqueous phase was transferred to the storage and disposal system. The organic phase was transferred to the reactor and the aqueous phase to the scrubber. To the scrubber was added 25cc of aqueous ammonia and 81 grams of butyraldehyde. The reactor was heated over a 2 hour period to 180° C. and the evolved gas and condensate collected in the scrubber. The reaction product was removed. This process was repeated 6 more times. The total amount of butyraldehyde used was 567 grams. The combined yields were 430 grams of a mixture of 1-Butyl 2-propyl 3,5-diethyl 1,2-dihydropyridine and 2-propyl 3,5-diethylpyridine (92.8% of theory).

According to the method described in examples 1–5, several aldehydes and mixed aldehydes were reacted. The results are summarized in Table I.

Table I

| Ex. No. | Aldehyde(s) Used | Method as described in Ex. No. | Product |
|---|---|---|---|
| 7 | Propionaldehyde | 1 | 1-propyl 2-ethyl 3,5-dimethyl 1,2-dihydropyridine and 2-ethyl 3,5-dimethylpyridine |
| 8 | Propionaldehyde | 2 | N-Propyl 2-ethyl 3,5-dimethyl pyridinium acetate and 2-ethyl 3,5-dimethylpyridine |
| 9 | Propionaldehyde | 3 | 2-Ethyl 3,5-dimethylpyridine |
| 10 | Valeraldehyde | 1 | 1-Pentyl 2-butyl 3,5-dipropyl 1,2-dihydropyridine and 2-butyl 3,5-dipropylpyridine |
| 11 | Valeraldehyde | 3 | 2-Butyl 3,5-dipropylpyridine |
| 12 | Propionaldehyde and butyr- | | Mixture of N-substituted alkyl-dihydropyridines and alkyl- |

Table I-continued

| Ex. No. | Aldehyde(s) Used | Method as described in Ex. No. | Product |
|---|---|---|---|
| | aldehyde | 1 | substituted pyridines |

USE AS CORROSION INHIBITORS

This phase of this invention relates to the use of these compounds in inhibiting the corrosion of metals, most particularly iron, steel and ferrous alloys. These compounds can be used in a wide variety of applications and systems where iron, steel and ferrous alloys are affected by corrosion. They may be employed for inhibiting corrosion in processes which require a protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is on contact with a corrosive oil-containing medium, as, for example, in oil wells producing corrosive oil or oil-brine mixtures, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2$, air or oxygen, etc.

The method of carrying out this process is relatively simple in principle. The corrosion preventive compound is dissolved in the liquid corrosive medium in small amounts and is thus kept in contact with the metal surface to be protected. Alternatively, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, air or oxygen, organic acids and the like. For the protection of such wells, the compound, either undiluted or dissolved in a suitable solvent, is fed down the annulus of the well between the casing and producing tubing where it becomes commingled with the fluid in the well and is pumped or flowed from the well with these fluids, thus contacting the inner wall of the casing, the outer and inner wall of tubing, and the inner surface of all wellhead fittings, connections and flow lines handling the corrosive fluid.

Where the inhibitor composition is a liquid, it is conventionally fed into the well annalus by means of a motor driven chemical injector pump, or it may be dumped periodically (e.g., once every day or two) into the annulus by means of a so-called "boll weevil" device or similar arrangement. Where the inhibitor is a solid, it may be dropped into the well as a solid lump or stock, it may be blown in as a powder with gas, or it may be washed in with a small stream of the well fluids or other liquid. Where there is gas pressure on the casing, it is necessary of course, to employ any of these treating methods through a pressure equalizing chamber equipped to allow introduction of reagent into the chamber, equalization of pressure between chamber and casing, and travel of reagent from chamber to well casing.

Occasionally, oil and gas wells are completed in such a manner that there is no opening between the annulus and the bottom of the tubing or pump. This results, for example, when the tubing is surrounded at some point by a packing held by the casing or earth formation below the casing. In such wells the compound may be introduced into the tubing through a pressure equalizing vessel, after stopping the flow of fluids. After being so treated, the well should be left closed in for a period of time sufficient to permit the reagent to drop to the bottom of the well.

For injection into the well annulus, the corrosion inhibitor is usually employed as a solution in a suitable solvent. The selection of solvent will depend much upon the specific compound being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described compounds appears to be maintained for an appreciable time after treatment ceases, but eventually is lost unless another application is made.

For example, for the protection of gas wells and gas-condensate wells, the amount of corrosion inhibitor used might range between about ¼ to 3 lbs. per million cubic feet of gas produced, depending upon the amounts and composition of corrosive agents in the gas and the amount of liquid hydrocarbon and water produced. However, in no case does the amount of inhibitor required appear to be stoichiometrically related to the amount of acids produced by a well, since protection is obtained with much less corrosion inhibitor than usually would be required for neutralization of the acids produced.

These compounds are particularly effective in the prevention of corrosion in systems containing a corrosive aqueous medium, and most particularly in system containing brines.

These compounds can also be used in the prevention of corrosion in the secondary recovery of petroleum by water flooding and in the disposal of waste water and brine from oil and gas wells. Still more particularly, they can be used in a process of preventing corrosion in water flooding and in the disposal of waste water and bring from oil and gas wells which is characterized by injecting into an underground formation an aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increses the cost thereof by making it necessary to repair and replace such equipment at frequent intervals.

We have discovered a method of preventing corrosion in systems containing a corrosive aqueous media, and most particularly in systems containing brines, which is characterized by employing the compounds described herein. For example, we have discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation an aqueous solution of the compositions of this invention.

The invention, then, is particularly concerned with preventing corrosion in a water flooding process characterized by the flooding medium, containing an aqueous or an oil field brine solution of these reagents.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compounds of this invention can also be used in such water disposal wells thus providing a simple and economical method of solving the corrosion problems encountered in disposing of unwanted water.

Water flood and waste disposal operations are too well known to require further elaboration. In essence, the flooding operation is effected in the conventional manner except that the flooding medium contains a minor amount of these compounds, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc. and in conjunction with other secondary recovery methods.

The concentration of the corrosion inhibitors of this invention will vary widely depending on the particular compound, the particular system, etc. Concentration of at least about ¼ p.p.m., such as about ¼ to 7,500 p.p.m., for example about 1 to 5,000 p.p.m., advantageously about 10 to 1,000 p.p.m., but preferably about 15–250 p.p.m. may be employed. Larger amounts can also be employed such as 1.5–5.0% although these is generally no commercial advantage in so doing.

For example, since the success of a water flooding operation manifestly depends upon its total cost being less than the value of the additional oil recovered from the oil reservoir, it is quite important to use as little as possible to these compounds consistent with optimum corrosion inhibition. Since these compounds are themselves inexpensive and are used in low concentrations, they enhance the success of a flood operation by lowering the cost thereof.

By varying the constituents of the composition, the compounds of this invention can be made more oil or more water soluble, depending on whether the composition is to be employed in oil or water systems.

Although the manner of practicing the present invention is clear from the foregoing description, the following non-limiting specific examples are included for purposes of illustration.

CORROSION TESTS

The test procedure includes measurement of the corrosive action of fluids inhibited by the compositions herein upon sand-blasted SAE-1020 steel coupons under accelerating conditions.

In the test a container is charged with 20% (wt.) sulfuric acid, 0.25% of chemical and the acid solution heated to 195° F. Pre-weighted steel coupons are emerged in the acid solution for 15 minutes and the weight loss is determined. Percent protection is calculated from $$\frac{R_1 - R_2}{R_1} \times 100\%$$

where $R_1$ is corrosion rate of uninhibited fluids, where $R_2$ is corrosion rate of inhibited fluids.

The results are presented in Table II

Table II

| Product of Example | Percent Protection |
|---|---|
| 1 | 85.5 |
| 2 | 91.5 |
| 3 | 88.8 |
| 4 | 85.5 |
| 5 | 86.2 |
| 6 | 89.4 |
| 7 | 86.3 |
| 8 | 86.2 |

Table II-continued

| Product of Example | Percent Protection |
| --- | --- |
| 9 | 86.3 |
| 10 | 91.6 |
| 11 | 91.3 |
| 12 | 90.2 |

We claim:

1. A process of preparing a mixture of an alkyl pyridine and an N-substituted alkyl 1,2-dihydropyridine which comprises reacting a hexahydrotriazine in the presence of a Lewis acid at a temperature between about 80° C, and 300° C. for a period of about 0.5 to 24 hours.

2. The process of claim 1 wherein the products obtained therein are further reacted with an acid in the presence of oxygen to obtain a mixture of an alkylpyridine and an N-substituted alkylpyridinium salt.

3. The process of claim 2 where the alkyl pyridinium salt is further thermally reacted to form an alkylpyridine.

4. The process of claim 1 wherein the mixture of alkylpyridine and N-substituted alkyl 1,2-dihydropyridine is further reacted to form a mixture of alkylpyridine and the Diels-Alder dimer of the 1,2-dihydropyridine.

5. The product of claim 1.

6. The product of claim 2.

7. The product of claim 3.

8. The product of claim 4.

9. The process of claim 1 where the temperature of reaction is about 110° C, to 180° C. and the time of reaction is from about 2 to 4 hours.

10. The process of claim 2 where the acid used is selected from the group consisting of sulfuric acid, hydrochloric acid, hydrobromic acid, acetic acid, proprionic acid, benzoic acid and sulfonic acids.

11. The process of claim 1 where the hexahydrotriazine is 2,4,6-tripropyl 1,3,5-hexahydrotriazine, the alkylpyridine is 2-propyl 3,5-diethylpyridine and the dihydropyridine is 1-butyl 2-propyl 3,5-diethyl 1,2-dihydropyridine.

12. The process of claim 4 where the alkyl pyridine is 2-propyl 3,5-diethyl pyridine, the 1,2-dihydropyridine is 1-butyl 2-propyl 3,5-diethyl 1,2-dihydropyridine, the reaction is carried out at 245° C. for five hours and the resulting product is a mixture of 2-propyl 3,5-diethyl pyridine and the Diels-Alder dimer of 1-butyl, 2-propyl 3,5-diethyl 1,2-dihydropyridine.

* * * * *